(12) United States Patent
Magnuson et al.

(10) Patent No.: US 8,088,233 B2
(45) Date of Patent: Jan. 3, 2012

(54) METHOD OF CHARACTERIZING PHASE TRANSFORMATIONS IN SHAPE MEMORY MATERIALS

(75) Inventors: Mark A. Magnuson, Bloomington, IN (US); Frank J. Liu, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 525 days.

(21) Appl. No.: 12/274,556

(22) Filed: Nov. 20, 2008

(65) Prior Publication Data

US 2009/0139614 A1    Jun. 4, 2009

Related U.S. Application Data

(60) Provisional application No. 60/992,258, filed on Dec. 4, 2007.

(51) Int. Cl.
*C21D 11/00* (2006.01)
*C22F 1/10* (2006.01)

(52) U.S. Cl. .................................. 148/508; 148/563

(58) Field of Classification Search .................... None
See application file for complete search history.

(56) References Cited

U.S. PATENT DOCUMENTS

| 4,881,981 | A * | 11/1989 | Thoma et al. ............. | 148/563 |
| 6,149,742 | A * | 11/2000 | Carpenter et al. ........ | 148/563 |
| 6,689,486 | B2 * | 2/2004 | Ho et al. .................... | 428/610 |
| 2008/0215131 | A1 * | 9/2008 | Magnuson et al. ....... | 623/1.12 |
| 2010/0016952 | A1 * | 1/2010 | Prokoshkin et al. ..... | 623/1.18 |

OTHER PUBLICATIONS

International Search Report and Written Opinion for PCT/US2008/085144 dated Jun. 16, 2009.
Liu, F.; Ding, Z.; Li, Y.; Xu, H. "Phase Transformation Behaviors and Mechanical Properties of TiNiMo Shape Memory Alloys," *Intermetallics*, 2005, 13, 357-360.
"Standard Test Method for Transformation Temperature of Nickel-Titanium Alloys by Thermal Analysis," *American Society for Testing and Materials (ASTM) Standard F2004-05*, ASTM International, West Conshohocken, PA, 2005, 4 pages.
"Standard Terminology for Nickel-Titanium Shape Memory Alloys," *American Society for Testing and Materials (ASTM) Standard F2005-05*, ASTM International, West Conshohocken, PA, 2005, 3 pages.

* cited by examiner

*Primary Examiner* — George Wyszomierski
(74) *Attorney, Agent, or Firm* — Brinks Hofer Gilson & Lione

(57) ABSTRACT

A method of characterizing phase transformations of a shape memory material specimen entails recording data from the specimen during heating and cooling. The temperature of the specimen is changed in a first direction to a first temperature sufficient to define a first inflection and a second inflection in the data being recorded. The temperature of the specimen is changed in a second direction to a second temperature sufficient to define a third inflection in the data. The third inflection is formed by overlapping primary and secondary sub-inflections. The temperature of the specimen is changed in the first direction to a third temperature sufficient to define the first inflection but not sufficient to define the second inflection. The temperature of the specimen is then changed in the second direction to a fourth temperature sufficient to define the secondary sub-inflection in the data being recorded.

18 Claims, 6 Drawing Sheets

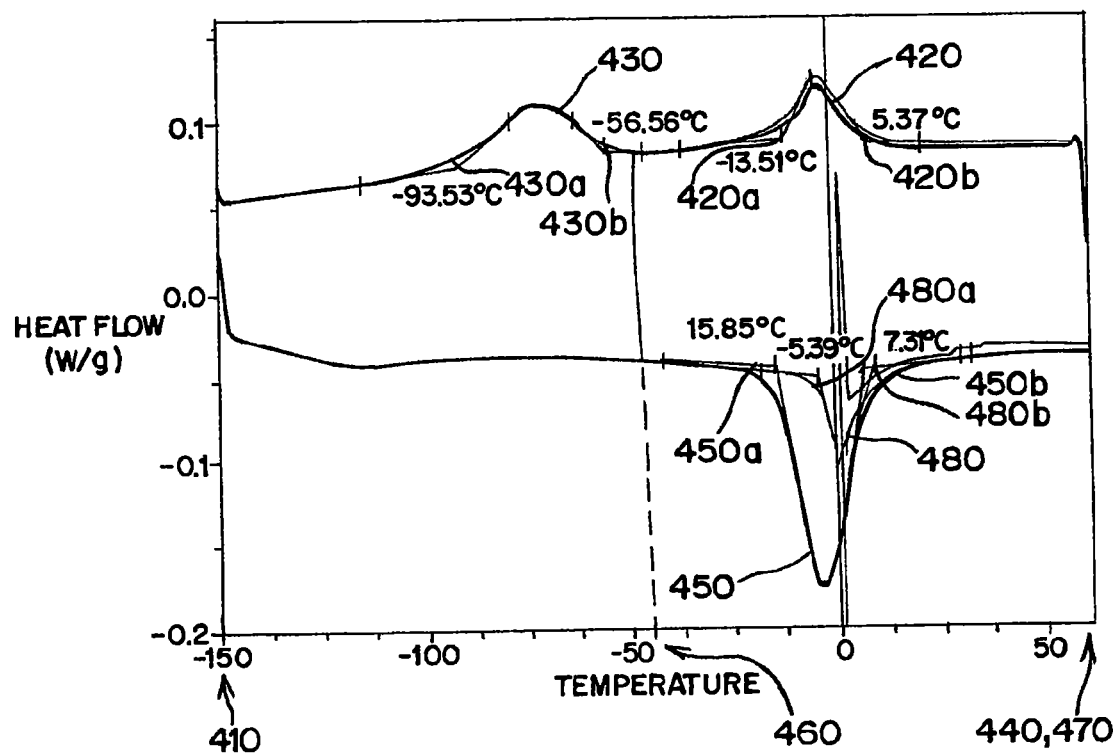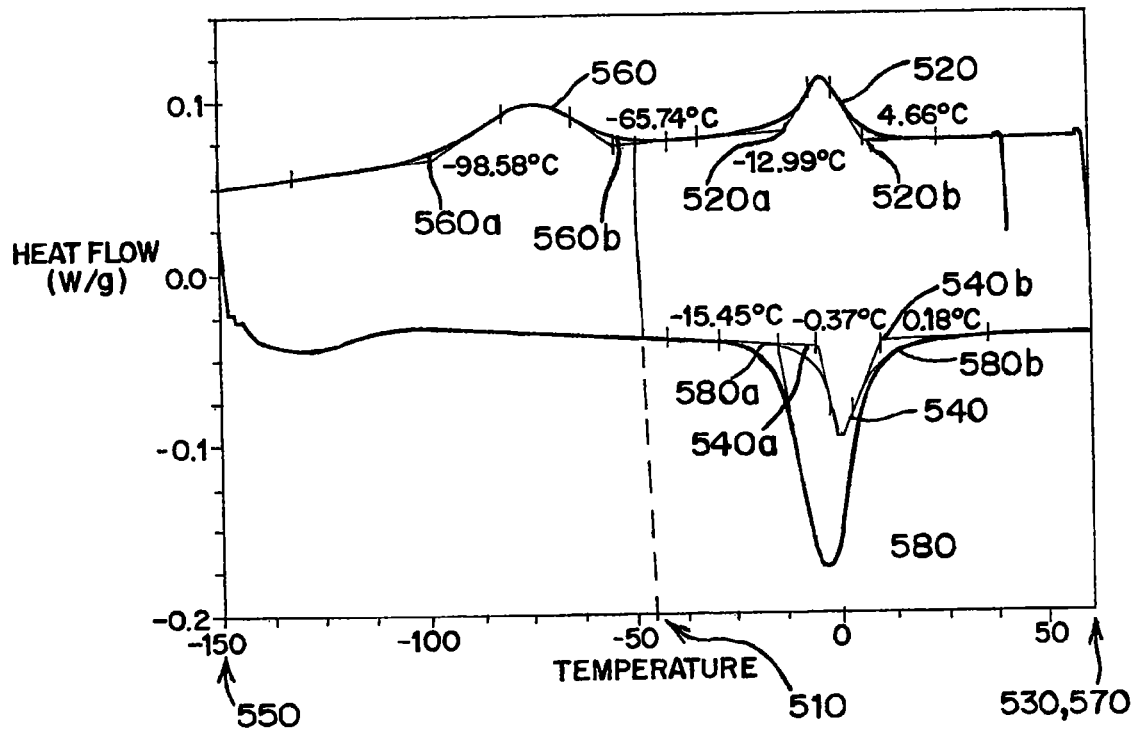

METHOD OF CHARACTERIZING PHASE TRANSFORMATIONS IN SHAPE MEMORY MATERIALS

RELATED APPLICATION

The present patent document claims the benefit of the filing date under 35 U.S.C. §119(e) of U.S. Provisional Patent Application Ser. No. 60/992,258, which was filed on Dec. 4, 2007, and is hereby incorporated by reference in its entirety.

TECHNICAL FIELD

The present disclosure is related generally to methods of characterizing materials, and more particularly to a method of characterizing phase transformations in shape memory materials.

BACKGROUND

Many medical devices rely on engineered materials such as polymers and metal alloys to perform various functions in the human body. In designing and developing medical devices, it is important to understand the characteristics and properties of the component materials so that an accurate prediction of material response during manufacturing and usage can be ascertained. An understanding of material behavior can be critical to identifying specific process controls, such as temperature control, needed to ensure that the material response is both predictable and repeatable with a high confidence level.

Typically, a variety of testing techniques are employed to aid in characterizing engineered materials. For example, differential scanning calorimetry (DSC), dynamic mechanical analysis (DMA), tensile testing and other methods can be used to determine various material characteristics, including phase transformation temperatures and mechanical properties.

Phase transformation temperature determination is an important aspect of material characterization for polymers and metals. DSC is an industry standard test method used to determine melt/glass transition temperatures for polymers and phase transformation temperatures for metals. In particular, the technique is widely used to identify phase transformations in nickel-titanium shape memory alloys, typically in accordance with ASTM Standard F 2004-05, "Standard Test Method for Transformation Temperature of Nickel-Titanium Alloys by Thermal Analysis," which is hereby incorporated by reference in its entirety.

Nickel-titanium shape memory materials reversibly transform between a lower temperature phase (martensite) and a higher temperature phase (austenite). The forward and reverse phase transformations may be driven by the application and removal of stress (superelastic effect) and/or by a change in temperature (shape memory effect). Austenite is characteristically the stronger phase, and martensite may be deformed up to a recoverable strain of about 8%. Strain introduced in the alloy in the martensitic phase to achieve a shape change may be recovered upon completion of a reverse phase transformation to austenite, allowing the material to return to a previous shape.

Some nickel-titanium shape memory alloys may exhibit a two-stage transformation which includes a transformation to a rhombohedral phase (R-phased) in addition to the monoclinic (B12) martensitic phase and the cubic (B2) austenitic phase. The transformation to R-phase in two-stage shape memory materials occurs prior to the martensitic transformation upon cooling and prior to the austenitic transformation upon heating.

As generally understood by those skilled in the art, martensite start temperature ($M_s$) refers to the temperature at which the phase transformation to martensite begins upon cooling, and martensite finish temperature ($M_f$) refers to the temperature at which the phase transformation to martensite concludes. Austenite start temperature ($A_s$) refers to the temperature at which the phase transformation to austenite begins upon heating, and austenite finish temperature ($A_f$) refers to the temperature at which the phase transformation to austenite concludes. R-phase start temperature ($R_s$) refers to the temperature at which a phase transformation to R-phase begins upon cooling for a two-stage shape memory material, and R-phase finish temperature ($R_f$) refers to the temperature at which the phase transformation to R-phase concludes upon cooling. Finally, R'-phase start temperature ($R'_s$) is the temperature at which a phase transformation to R-phase begins upon heating for a two-stage shape memory material, and R'-phase finish temperature ($R'_f$) is the temperature at which the phase transformation to R-phase concludes upon heating.

The DSC test method involves heating and cooling a test specimen at a controlled rate in a controlled environment through the temperature intervals of the phase transformations. The difference in heat flow between the test material and a reference due to energy changes is continuously monitored and recorded. Absorption of energy due to a phase transformation in the specimen results in an endothermic valley on heating. Release of energy due to a phase transformation in the specimen results in an exothermic peak upon cooling. Phase transformation temperatures (e.g., $M_s$, $M_f$, $R_s$, $R_f$, etc.) can be obtained from the DSC data by determining the start and finish of each transformation.

ASTM Standard F 2005-05, "Standard Terminology for Nickel-Titanium Shape Memory Alloys," illustrates exemplary DSC graphs for shape memory alloys exhibiting a single-stage or a two-stage transformation. These DSC graphs are reproduced as FIGS. 1 and 2 in the present patent document. A shape memory alloy exhibiting a single-stage transformation undergoes a one-step change between austenite and martensite in response to a variation in temperature. During cooling, the alloy transforms from austenite to martensite, and during heating, the alloy transforms from martensite to austenite. Accordingly, the DSC graph of FIG. 1 shows a single peak during cooling and a single valley during heating corresponding to the respective transformations.

A shape memory alloy exhibiting a two-stage transformation undergoes a two-step change in crystallographic structure involving austenite, martensite, and R-phase in response to a variation in temperature. During cooling, the alloy transforms from austenite to R-phase (first peak), and then from R-phase to martensite (second peak), as shown in FIG. 2. During heating, the alloy transforms from martensite to R-phase (first valley), and then from R-phase to austenite (second valley) during heating.

Both in practice and in some of the scientific literature, DSC testing of some nickel-titanium shape memory alloys reveals two peaks 310, 320 during cooling but only a single valley 330 during heating, as shown in FIG. 3. It is accepted by some that the two peaks observed during cooling correspond to a two-stage transformation from austenite to R-phase and from R-phase to martensite, while the single valley observed during heating corresponds to a one-step phase change from martensite to austenite. That is, some believe that a nickel-titanium shape memory alloy may exhibit a forward transformation to R-phase during cooling without exhibiting a reverse transformation to R-phase during heating. Others believe that a two-stage reverse transformation may in fact occur during heating, despite the appearance of only a single valley in the DSC data. However, due to the overlapped nature of the valley and the shortcomings of the testing protocol specified in ASTM Standard F 2004-05, the two-stage reverse transformation cannot be fully defined using present methods of DSC testing. Accordingly, phase transformation temperatures, in particular $R'_f$ and $A_s$, can only be estimated.

Since an understanding of the phase transformations occurring in shape memory alloys may be critically important for medical and other applications of these alloys, a better method of characterizing phase transformations and determining phase transformation temperatures of these materials is desired.

BRIEF SUMMARY

Described herein is an improved method of characterizing phase transformations in shape memory materials. The method is particularly advantageous for shape memory alloys comprising an R-phase transformation. The method allows overlapping inflections in differential scanning calorimetry (DSC) or other data to be deconvoluted into sub-inflections that represent distinct phase transformations. Accordingly, the method described herein may allow phase transformation temperatures, such as $A_s$ and $R'_f$, to be unambiguously determined for shape memory alloys having an R-phase transformation.

According to one embodiment, the method entails recording data from a specimen comprising a shape memory material during heating and cooling. The temperature of the specimen is changed in a first direction to a first temperature which is sufficient to define a first inflection and a second inflection in the data being recorded. The first inflection occurs over a first temperature interval, and the second inflection occurs over a second temperature interval. The temperature of the specimen is changed in a second direction to a second temperature which is sufficient to define a third inflection in the data being recorded. The third inflection occurs over a third temperature interval and is formed by overlapping primary and secondary sub-inflections. The temperature of the specimen is changed in the first direction to a third temperature which is sufficient to define the first inflection in the data being recorded but not sufficient to define the second inflection. The temperature of the specimen is then changed in the second direction to a fourth temperature sufficient to define the secondary sub-inflection in the data being recorded.

According to another embodiment, the method comprises recording data from a specimen comprising a shape memory alloy during heating and cooling, where the specimen has an R-phase transformation. The specimen is cooled to a first temperature sufficient to define a first inflection and a second inflection in the data being recorded. The first inflection occurs over a first temperature interval and corresponds to a phase transformation from austenite to R-phase, and the second inflection occurs over a second temperature interval and corresponds to a phase transformation from R-phase to martensite. The specimen is heated to a second temperature sufficient to define a third inflection in the data being recorded, where the third inflection occurs over a third temperature interval and is formed by overlapping primary and secondary sub-inflections corresponding respectively to phase transformations from martensite to R-phase and from R-phase to austenite. The specimen is cooled to a third temperature sufficient to define the first inflection but not sufficient to define the second inflection, whereby the shape memory alloy has a substantially fully R-phase structure. The specimen is then heated to a fourth temperature sufficient to define the secondary sub-inflection in the data being recorded, where the secondary sub-inflection corresponds to the phase transformation from R-phase to austenite.

According to another embodiment, the method comprises recording data from a specimen comprising a shape memory alloy during heating and cooling, where the specimen has an R-phase transformation, and cooling the specimen to a first temperature sufficient to define only a first inflection in the data being recorded. The first inflection occurs over a first temperature interval and corresponds to a phase transformation from austenite to R-phase. The specimen is heated to a second temperature sufficient to define a second inflection in the data being recorded, where the second inflection occurs over a second temperature interval and corresponds to a phase transformation from R-phase to austenite. At least one of an austenite start temperature and an austenite finish temperature of the shape memory alloy are determined from the second inflection.

BRIEF DESCRIPTION OF THE DRAWINGS

FIG. 4 is a DSC graph generated by a double-loop experiment, according to a first embodiment, for the third exemplary shape memory alloy;

FIG. 5 is a DSC graph generated by a double-loop experiment, according to a second embodiment, for the third exemplary shape memory alloy;

DETAILED DESCRIPTION

Figure 3:
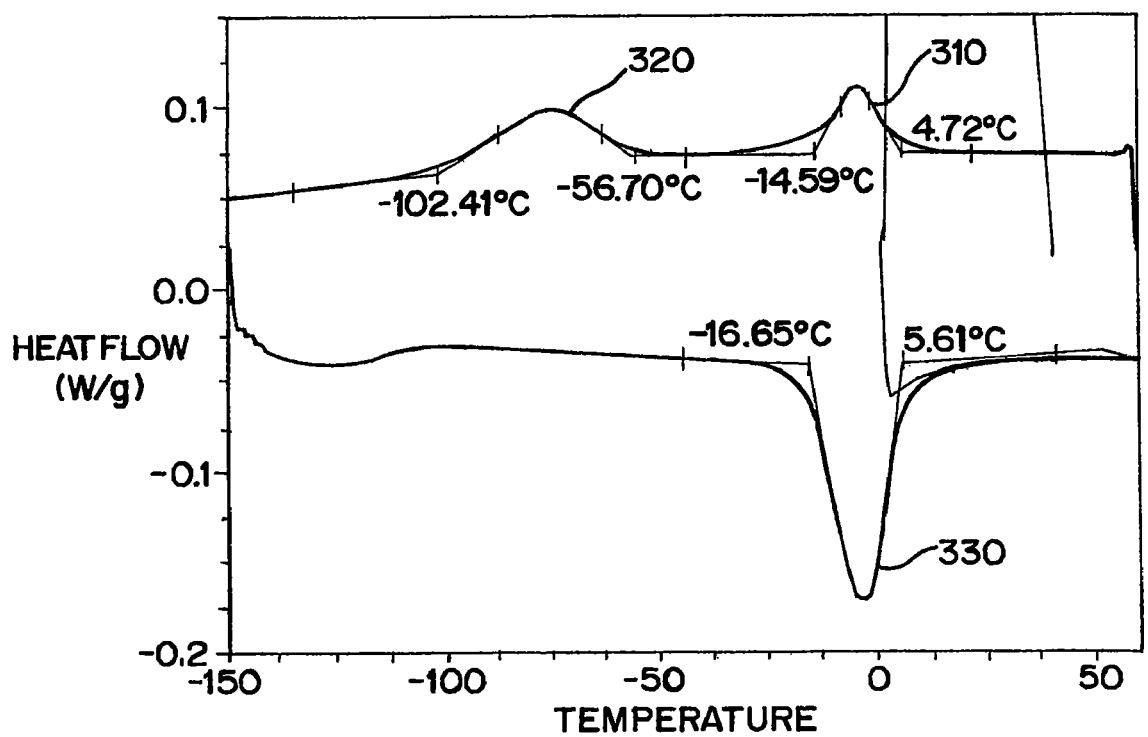
FIG. 3 is a DSC graph for a third exemplary shape memory alloy exhibiting a two-stage transformation.

FIG. 3 shows DSC data obtained from a conventional (single-loop) experiment carried out on a nickel-titanium alloy specimen including an R-phase transformation. As discussed previously, two peaks 310, 320 in the data are obtained during cooling, but only a single valley 330 is obtained during heating. As noted previously, peaks are formed during cooling in the DSC data because the phase transformations that occur are exothermic. In other words, heat is released as the shape memory alloy transforms from one phase to another. In contrast, endothermic valleys or sub-valleys are formed in the DSC data during heating because heat is absorbed by the specimen as the shape memory alloy changes phase.

Figure 8:
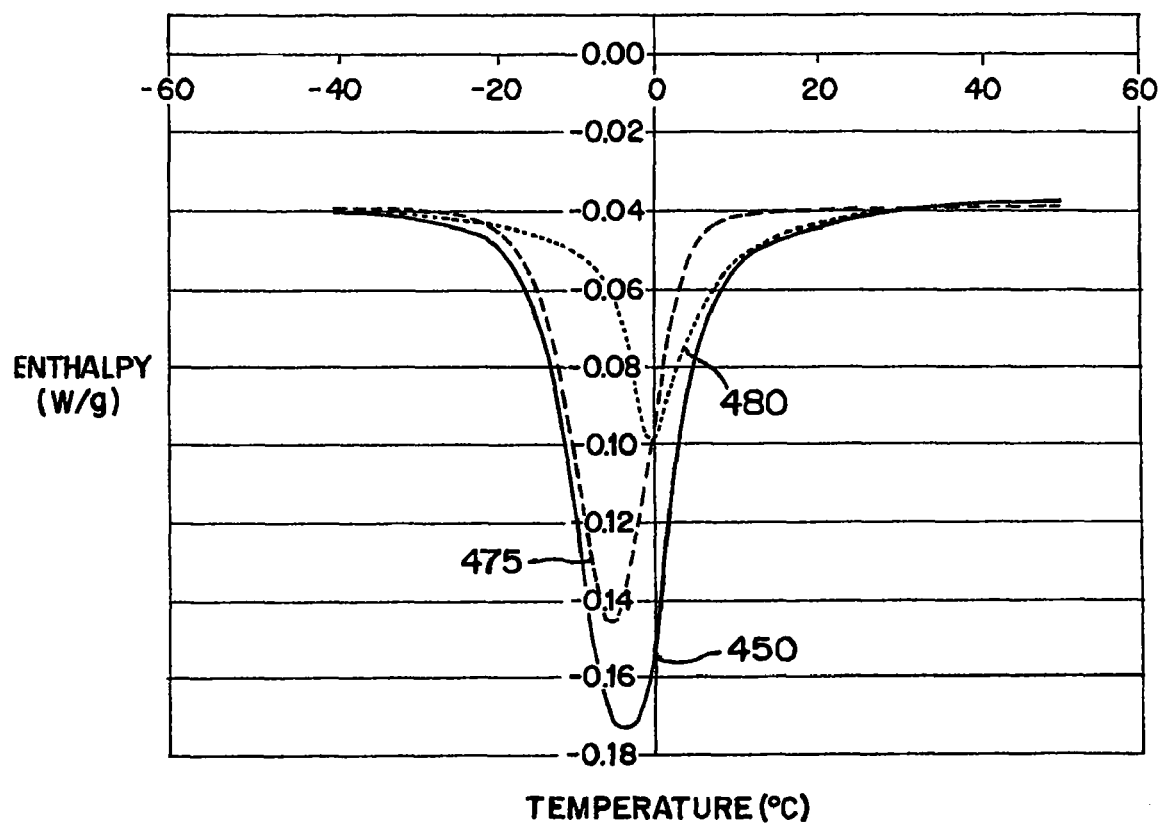
FIG. 8 is a graph showing an overlapped valley deconvoluted into a first sub-valley and a second sub-valley according to the experimental and computational protocol set forth herein.

FIGS. 4 and 5 show DSC data generated through a double-loop experiment for the same specimen that generated the data of FIG. 3. In the DSC data of FIG. 4, for example, two peaks 420, 430 are obtained during cooling, and a valley 450 and a sub-valley 480 are obtained during heating. The sub-valley 480 overlaps with an additional sub-valley that may be defined computationally using the data from the double-loop experiment. The valley 450 is formed by the overlap of the sub-valleys 475, 480 as shown in FIG. 8, and thus may be referred to as an overlapped valley 450. In addition, the computationally defined sub-valley 475 may be referred to as a first sub-valley 475, and the experimentally determined sub-valley 480 may be referred to as a second sub-valley 480. (This nomenclature is chosen due to the order in which the phase transformations corresponding to the respective sub-valleys 475, 480 occur during heating.)

By employing the double-loop DSC experiment described herein according to two embodiments, it is possible to isolate the second sub-valley 480 corresponding to the R-phase to austenite phase transformation from the overlapped valley 450 obtained during a single DSC loop. Using these DSC data, it is further possible to computationally define the first sub-valley 475 of the overlapped valley 450 corresponding to the martensite to R-phase transformation. Thus, by combining the experimental double-loop method with computational analysis, an overlapped valley 450 may be unambiguously separated into its component first and second sub-valleys 475, 480. Accordingly, phase transformations for a shape memory alloy exhibiting an R-phase transformation may be properly characterized, and phase transformation temperatures (e.g., $R'_s$, $R'_f$, $A_s$ and $A_f$) may be accurately determined.

Double-Loop Experiment

First Exemplary Embodiment

Figure 6:
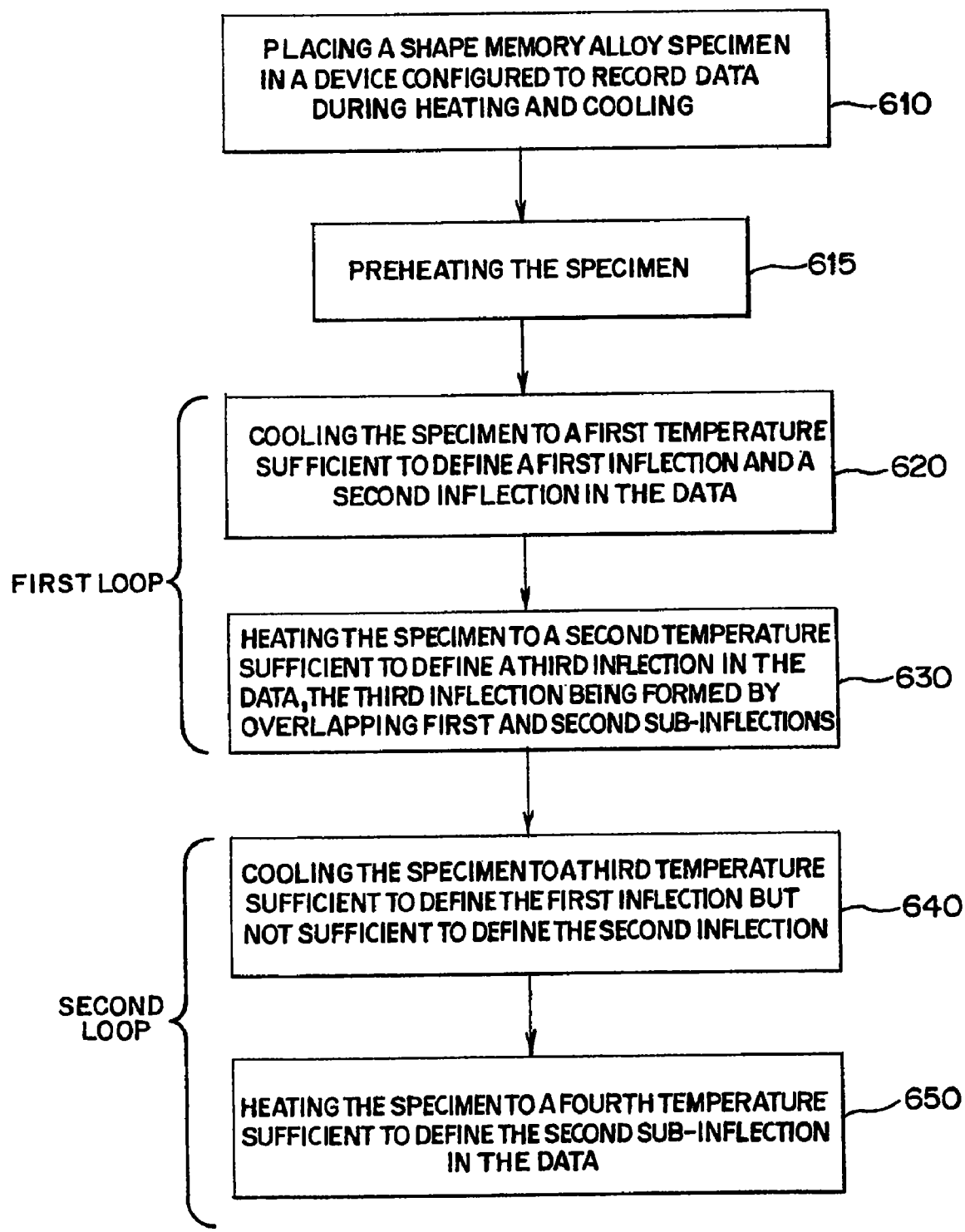
FIG. 6 is a flow chart showing steps of the first embodiment of the double loop experiment.

FIG. 6 is a flow chart showing steps of the first embodiment of the double-loop method. Referring to the flow chart, a specimen comprising a shape memory alloy having an R-phase transformation is placed 610 in a device configured to record data during heating and cooling. Preferably, the device is a differential scanning calorimeter and the data recorded are heat flow as a function of temperature. The specimen is cooled 620 to a first temperature sufficient to define a first inflection and a second inflection in the data. The first inflection occurs over a first temperature interval and corresponds to a phase transformation from austenite to R-phase, and the second inflection occurs over a second temperature interval and corresponds to a phase transformation from R-phase to martensite. The specimen is then heated 630 to a second temperature sufficient to define a third inflection in the data. Preferably, the specimen is substantially fully austenitic at the second temperature. The third inflection occurs over a third temperature interval and is formed by overlapping primary and secondary sub-inflections corresponding, respectively, to phase transformations from martensite to R-phase and from R-phase to austenite. Cooling to the first temperature and heating to the second temperature constitute the first loop of the DSC experiment. The specimen is then cooled 640 to a third temperature between the first inflection and the second inflection, whereby the shape memory alloy has a substantially fully R-phase structure, and the specimen is heated 650 to a fourth temperature sufficient to define the secondary sub-inflection in the data corresponding to the phase transformation from R-phase to austenite. Cooling to the third temperature and heating to the fourth temperature constitute the second loop of the DSC experiment. Data are recorded throughout the test.

The inflections and sub-inflections in the data can generally be defined as substantial departures from a baseline of the data. For example, the inflections and sub-inflections are significant enough to be distinguished from noise in the data. In the case of the exemplary DSC data discussed herein, such as that shown in FIGS. 1-5, the inflections in the data are the peaks and valleys (or sub-valleys) that occur over various temperature intervals. In other types of data that may be obtained from shape memory alloys as a function of temperature, such as, for example, electrical resistivity data, the inflections in the data may take the form of bends or changes in slope with respect to the baseline.

The first embodiment of the double loop experiment is described in detail in reference to FIGS. 4 and 6. A nickel-titanium shape memory alloy specimen having an R-phase transformation is placed 610 in a differential scanning calorimeter such as, for example, DSC Model Q10 from TA Instruments. Preparation of the specimen and the apparatus is generally carried out in accordance with ASTM Standard 2004-05, except that the specimen is preferably not annealed at 800° C. to 850° C. prior to testing. The anneal is generally not carried out so as to avoid changing or destroying microstructural features imparted to the specimen during prior thermomechanical processing.

Prior to beginning the first loop of the double loop experiment, a preheat step 615 may be carried out to ensure that the specimen is at least partly austenitic. Preferably, the shape memory alloy specimen is fully austenitic prior to cooling 620 to ensure that the phase transformation from austenite may be fully defined. If the specimen has an $A_f$ value below room temperature, the specimen may be fully austenitic at room temperature. Otherwise, it may be desirable to heat the specimen to a preheat temperature at which the shape memory alloy has an austenitic structure. It may be possible to determine the appropriate preheat temperature in situ by recording data showing heat flow as a function of temperature during the preheat step. If the specimen is not fully austenitic prior to heating, an endothermic valley in the data indicative of transformation of at least part of the specimen to austenite may be formed. For some specimens, the $A_f$ value of the specimen may be known, at least approximately, prior to testing. The preheat temperature may thus be selected to be above the temperature at which the valley appears to be fully formed during heating or above the known $A_f$ value. For example, the preheat temperature may be selected to be at least 30° C. above $A_f$, consistent with the ASTM Standard 2004-05. In another example, the preheat temperature may at least about 30° C. above the temperature at which the valley appears to be fully formed during heating, or 10° C. above this temperature. According to other embodiments, the preheat temperature may be at least about 40° C., or at least about 50° C., or at least about 60° C. Other preheat temperatures are possible also.

It is also preferred that the preheat temperature is maintained for a time sufficient for the specimen to equilibrate at that temperature. For example, the specimen may be heated to the preheat temperature and held at that temperature for a period of from about 30 seconds to about 90 seconds. Preferably, the specimen is held at the preheat temperature for about 60 seconds. Other hold times may also be employed.

After optionally preheating 615 the specimen as described above, the specimen is cooled 620 to a first temperature 410 sufficient to define both a first peak 420 and a second peak 430 in the data. As noted above, the first peak 420 corresponds to the phase transformation of the shape memory alloy from austenite to R-phase, and it occurs over a first temperature interval. The second peak 430 corresponds to the phase transformation from R-phase to martensite and occurs over a second, lower temperature interval. Referring to FIG. 4, lower and upper boundaries 420a, 420b of the first temperature interval may be taken to be the phase transformation temperatures $R_f$ and $R_s$, respectively, and the lower and upper boundaries 430a, 430b of the second temperature interval may be taken to be approximately $M_f$ and $M_s$, respectively. (The formal determination of these phase transformation temperatures using a tangent technique is discussed below.) Preferably, cooling to the first temperature 410 is carried out at a rate consistent with that prescribed in ASTM Standard 2004-05. For example, the specimen may be cooled at a rate of about 10° C./min to the first temperature 410.

The first temperature 410 may be about $M_f$-30° C., consistent with ASTM Standard 2004-05. According to another embodiment, the first temperature 410 may be any temperature below the lower boundary 430*a* of the second temperature interval of the second peak 430, such as at least about 10° C. below the lower boundary 430*a*, or at least about 30° C. below the lower boundary 430*a*. In absolute terms, the first temperature 410 may be at most about 180° C., at most about 150° C., at most about 130° C. or at most about another temperature that falls below the lower boundary 430*a* of the second temperature interval.

It is preferred that the specimen is held at the first temperature 410 for a time sufficient to equilibrate at that temperature. For example, the specimen may be held at the first temperature 410 for a period of from about 30 seconds to about 90 seconds. Preferably, the specimen is held at the first temperature 410 for about 60 seconds. Other hold times may also be employed.

After the specimen is maintained at the first temperature 410 as described above, the specimen may then be heated to a second temperature 440 sufficient to define at least one valley 450 in the data. The valley 450 occurs over a third temperature interval having a lower boundary 450*a* and an upper boundary 450*b*. Preferably, the specimen is fully austenitic at the second temperature 440.

The second temperature 440 may be about $A_f$+30° C., according to one embodiment. According to another embodiment, the second temperature 440 may be any temperature above the upper boundary 450*b* of the third temperature inverval corresponding to the valley 450, such as at least about 10° C. above the upper boundary 450*b*, or at least about 30° C. above the upper boundary 450*b*. In absolute terms, the second temperature 440 may be at least about 30° C., at least about 40° C., at least about 60° C. or at least about another temperature above the upper boundary 450*b* of the third temperature interval.

As noted previously, and as illustrated in FIG. 3, only a single valley 450 may be apparent from the DSC data upon heating to the second temperature 440 although the specimen has undergone phase transformations from martensite to R-phase and from R-phase to austenite. The single valley 450 may thus be referred to as an overlapped valley 450 since it is formed by overlapping first and second sub-valleys corresponding respectively to phase transformations from martensite to R-phase and from R-phase to austenite. These overlapping first and second sub-valleys are not apparent in the data obtained thus far from the first cooling-heating loop of the DSC experiment. The second cooling-heating loop of the test is designed to isolate and define the second sub-valley of the overlapped valley 450 obtained during the prior heating step. In other words, the R-phase to austenite transformation may be isolated in the DSC data by carrying out the second cooling-heating loop of the double-loop experiment.

The specimen is cooled 640 to a third temperature 460 between the first peak 420 and the second peak 430, where the shape memory alloy has a substantially fully R-phase structure. More specifically, the third temperature 460 is preferably selected to be between the lower boundary 420*a* of the first temperature interval corresponding to the first peak 420 and the upper boundary 430*b* of the second temperature interval corresponding to the second peak 430 (in other words, below about $R_f$ and above about $M_s$). According to one embodiment, the third temperature 460 is in the range of from about −50° C. to about −20° C.

Preferably, the cooling to the third temperature 460 is carried out at a rate consistent with that prescribed in ASTM Standard 2004-05. For example, the specimen may be cooled at a rate of about 10° C./min to the third temperature 460. It is also preferred that the specimen is held at the third temperature 460 for a time sufficient to equilibrate at that temperature. For example, the specimen may be held at the third temperature 460 for a period of from about 30 seconds to about 90 seconds. Preferably, the specimen is held at the third temperature 460 for about 60 seconds. Other hold times may also be employed.

Next, the specimen is heated 650 to a fourth temperature 470 sufficient to define the second sub-valley 480 in the data. Preferably, the specimen is austenitic at the fourth temperature 470. The second sub-valley 480 is formed by the transformation of the shape memory alloy from R-phase to austenite during heating, and it occurs over a fourth temperature interval. Referring to FIG. 4, lower and upper boundaries 480*a*, 480*b* of the fourth temperature interval may be taken to be the phase transformation temperatures $A_s$ and $A_f$. Since the specimen does not enter the martensite phase during the previous cooling step, no martensite exists in the specimen at this point, and no transformation from martensite to R-phase occurs upon heating. Thus, this portion of the double loop experiment allows the second sub-valley 480 corresponding to the R-phase to austenite transformation to be isolated. Accordingly, the transformation temperature $A_s$, which cannot be discerned from a conventional single-loop DSC test, can be determined.

The fourth temperature 470 may be about $A_f$+30° C., according to one embodiment. According to another embodiment, and consistent with the description of the second temperature 440, the fourth temperature 470 may be any temperature above the upper boundary 450*b* of the fourth temperature interval of the valley 450, such as at least about 10° C. above the upper boundary 450*b*, or at least about 30° C. above the upper boundary 450*b*. In absolute terms, the second temperature 470 may be at least about 30° C., at least about 40° C., at least about 60° C. or at least about another temperature above the upper boundary 450*b* of the valley 450.

Preferably, the heating 650 to the fourth temperature 470 is carried out at a rate consistent with that prescribed in ASTM Standard 2004-05. For example, the specimen may be heated at a rate of about 10° C./min to the fourth temperature 470. It is also preferred that the specimen is held at the fourth temperature 470 for a time sufficient to equilibrate at that temperature. For example, the specimen may be held at the fourth temperature 470 for a period of from about 30 seconds to about 90 seconds. Preferably, the specimen is held at the fourth temperature 470 for about 60 seconds. Other hold times may also be employed.

Second Exemplary Embodiment

Figure 7:
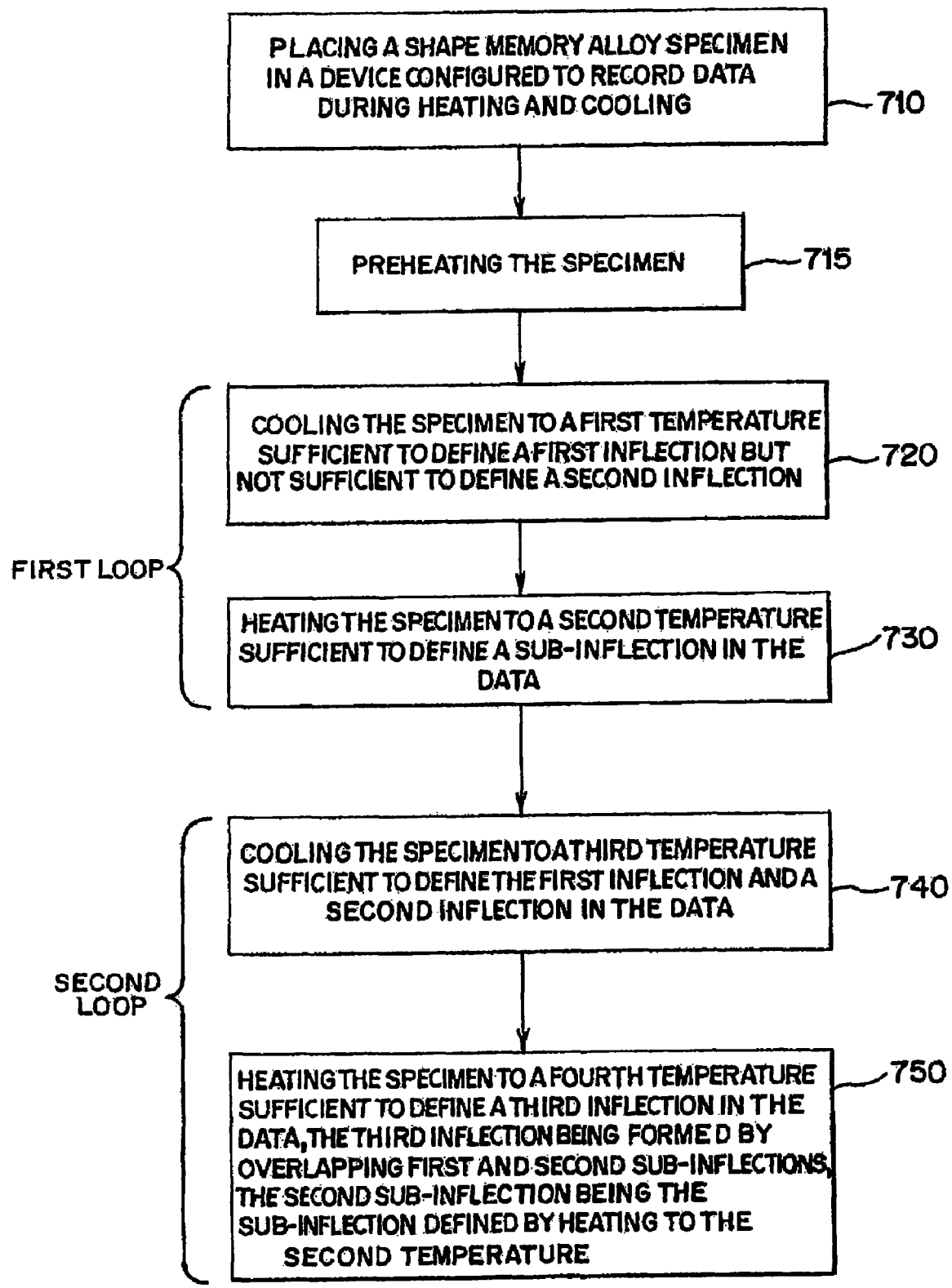
FIG. 7 is a flow chart showing steps of the second embodiment of the double loop experiment.

FIG. 7 is a flow chart showing steps of the second embodiment of the double-loop method. Referring to the flow chart, a specimen comprising a shape memory alloy having an R-phase transformation is placed 710 in a device configured to record data during heating and cooling. Preferably, the device is a differential scanning calorimeter and the data recorded are heat flow as a function of temperature. The specimen is cooled 720 to a first temperature sufficient to define only a first inflection in the data. The first inflection occurs over a first temperature interval and corresponds to a phase transformation from austenite to R-phase. The specimen is then heated 730 to a second temperature sufficient to define a sub-inflection in the data. The sub-inflection occurs over a second temperature interval and corresponds to a phase transformation from R-phase to austenite. Cooling to the first temperature and heating to the second temperature constitute the first loop of the DSC experiment. The specimen is then cooled 740 to a third temperature sufficient to define (redefine) the first inflection and to define a second inflection in the data, where the second inflection occurs over a third temperature interval and corresponds to a phase transformation from R-phase to martensite. Finally, the specimen is heated 750 to a fourth temperature sufficient to define a third inflection in the data. The third inflection occurs over a fourth temperature interval and is formed by overlapping primary and secondary sub-inflections corresponding respectively to phase transformations from martensite to R-phase and from R-phase to austenite. The sub-inflection defined by heating to the second temperature is the secondary sub-inflection. Cooling to the third temperature and heating to the fourth temperature constitute the second loop of the DSC experiment. Data are recorded throughout the test.

As mentioned above, the inflections and sub-inflections in the data can generally be defined as substantial departures from a baseline of the data. For example, the inflections and sub-inflections are significant enough to be distinguished from noise in the data. In the case of the exemplary DSC data discussed herein, such as that shown in FIGS. 1-5, the inflections in the data are the peaks and valleys (or sub-valleys) that occur over various temperature intervals. In other types of data that may be obtained from shape memory alloys as a function of temperature, such as, for example, electrical resistivity data, the inflections in the data may take the form of bends or changes in slope with respect to the baseline.

The first cooling-heating loop of the DSC experiment according to the second embodiment is designed to define and isolate the second sub-valley in the data corresponding to the phase transformation from R-phase to austenite on heating. In contrast, in the first embodiment of the double-loop experiment, the second sub-valley is defined during the second cooling-heating loop of the DSC test.

The second embodiment of the double loop experiment is described in detail in reference to FIGS. 5 and 7. A nickel-titanium shape memory alloy specimen having an R-phase transformation is placed 710 in a differential scanning calorimeter such as, for example, DSC Model Q10 from TA Instruments. Preparation of the specimen and the apparatus is generally carried out in accordance with ASTM Standard 2004-05, except that the specimen is preferably not annealed at 800° C. to 850° C. prior to testing. The anneal is generally not carried out so as to avoid changing or destroying microstructural features imparted to the specimen during prior thermomechanical processing.

A preheat step 715 may be carried out prior to initiating the first loop of the double loop experiment, as described in the previous embodiment. Thus, the description of the optional preheat step 715, which is designed to ensure that the specimen is austenitic prior to cooling, is not repeated here.

Referring to FIG. 5, the specimen is cooled 720 to a first temperature 510 sufficient to define only a first peak 520 in the data. In other words, the specimen is cooled to a first temperature below the first peak 520 but above a second peak (e.g., 560) that might be defined upon further cooling. The first peak 520 corresponds to a phase transformation from austenite to R-phase and occurs over a first temperature interval. Upper and lower boundaries 520a, 520b of the first temperature interval may be taken to be the phase transformation temperatures $R_f$ and $R_s$, respectively. At the first temperature 510, the specimen is preferably fully R-phase.

The first temperature 510 is preferably selected to be less than the lower boundary 520a of the first peak 520 but higher than an upper boundary of any additional peaks (e.g., R-phase to martensite) that develop upon cooling. That is, the first temperature is preferably below about $R_f$ but above the martensite start temperature, $M_s$. According to one embodiment, the first temperature 510 is in the range of from about −50° C. to about −20° C.

The cooling 720 to the first temperature 510 may be carried out at a rate consistent with that prescribed in ASTM Standard 2004-05. For example, the specimen may be cooled at a rate of about 10° C./min to the first temperature 510. It is also preferred that the specimen is held at the first temperature 510 for a time sufficient to equilibrate at that temperature. For example, the specimen may be held at the first temperature 510 for a period of from about 30 seconds to about 90 seconds. Preferably, the specimen is held at the first temperature 510 for about 60 seconds. Other hold times may also be employed.

Next, the specimen is heated 730 to a second temperature 530 sufficient to define a sub-valley (the second sub-valley) 540 in the data. The second sub-valley 540 is formed by the transformation of the shape memory alloy from R-phase to austenite during heating, and it occurs over a second temperature interval. Referring to FIG. 5, lower and upper boundaries 540a, 540b of the second temperature interval may be taken to be the phase transformation temperatures $A_s$ and $A_f$. Since the specimen does not enter the martensite phase during the previous cooling step, no martensite exists in the specimen at this point, and no transformation from martensite to R-phase occurs upon heating. Thus, this portion of the double loop experiment allows the second sub-valley 540 corresponding to the R-phase to austenite transformation to be isolated. Accordingly, the transformation temperature $A_s$, which cannot be discerned from a conventional single-loop DSC test, can be determined from these data.

The second temperature 530 may be about $A_f+30°$ C., according to one embodiment. According to another embodiment, the second temperature 530 may be any temperature above the upper boundary 540b of the second sub-valley 540, such as at least about 10° C. above the upper boundary 540b, or at least about 30° C. above the upper boundary 540b. In absolute terms, the second temperature 530 may be at least about 30° C., at least about 40° C., at least about 60° C., or at least about another temperature above the upper boundary 540b of the second sub-valley 540.

Preferably, the heating 730 to the second temperature 530 is carried out at a rate consistent with that prescribed in ASTM Standard 2004-05. For example, the specimen may be heated at a rate of about 10° C./min to the second temperature 530. It is also preferred that the specimen is held at the second temperature 530 for a time sufficient to equilibrate at that temperature. For example, the specimen may be held at the second temperature 530 for a period of from about 30 seconds to about 90 seconds. Preferably, the specimen is held at the second temperature 530 for about 60 seconds. Other hold times may also be employed.

The specimen is then cooled 740 to a third temperature 550 sufficient to redefine the first peak 520 and to define a second peak 560 in the data. As noted above, the first peak 520 corresponds to the phase transformation of the shape memory alloy from austenite to R-phase, and it occurs over the first temperature interval. The second peak 560 corresponds to the phase transformation from R-phase to martensite and occurs over a third, lower temperature interval. Referring to FIG. 5, lower and upper boundaries 520a, 520b of the first temperature interval may be taken to be the phase transformation temperatures $R_f$ and $R_s$, respectively, and the lower and upper boundaries 560a, 560b of the third temperature interval may be taken to be approximately $M_f$ and $M_s$, respectively. (The formal determination of these phase transformation temperatures using a tangent technique is discussed below.) Preferably, the cooling to the third temperature 550 is carried out at a rate consistent with that prescribed in ASTM Standard 2004-05. For example, the specimen may be cooled at a rate of about 10° C./min to the third temperature 550.

The third temperature 550 may be about $M_f$–30° C., according to one embodiment. According to another embodiment, the third temperature 550 may be any temperature below the lower boundary 560a of the third temperature interval corresponding to the second peak, such as at least about 10° C. below the lower boundary 560a, or at least about 30° C. below the lower boundary 560a. In absolute terms, the third temperature may be at most about 180° C., at most about 150° C., or at most about 130° C., or at most about another temperature that falls below the lower boundary 560a of the third temperature interval.

It is preferred that the specimen is held at the third temperature 550 for a time sufficient to equilibrate at that temperature. For example, the specimen may be held at the third temperature 550 for a period of from about 30 seconds to about 90 seconds. Preferably, the specimen is held at the third temperature 550 for about 60 seconds. Other hold times may also be employed.

After the specimen is held at the third temperature 550 as described above, the specimen may then be heated 750 to a fourth temperature 570 sufficient to define at least one valley 580 in the data. Preferably, the specimen is fully austenitic at the fourth temperature 570.

The fourth temperature 570 may be about $A_f$+30° C., according to one embodiment. According to another embodiment, the fourth temperature 550 may be any temperature above the upper boundary 580b of the fourth temperature interval corresponding to the valley 580, such as at least about 10° C. above the upper boundary 580b, or at least about 30° C. above the upper boundary 580b. In absolute terms, the fourth temperature 570 may be at least about 30° C., at least about 40° C., at least about 60° C., or at least about another temperature above the upper boundary 580b of the fourth temperature interval.

As noted previously, only a single valley 580 may be obtained upon heating 750 to the fourth temperature 570 although the specimen has undergone phase transformations from martensite to R-phase and from R-phase to austenite. The valley 580 may thus be referred to as an overlapped valley 580 formed by overlapping first and second sub-valleys corresponding respectively to phase transformations from martensite to R-phase and from R-phase to austenite. The second sub-valley 540 was defined experimentally in the first cooling-heating loop of the double-loop DSC experiment, according to this embodiment. The first sub-valley may be defined computationally, as described below, using the data obtained from the double-loop DSC test.

Computational Approach Using Data From Double-Loop Experiment

The computational approach to defining the martensite to R-phase transformation (i.e., the first sub-valley) uses the recorded data from the double-loop experiment, which was described above according to two embodiments. Recall that the double-loop experiment allows the second sub-valley corresponding to the R-phase to austenite transformation to be defined and isolated. The double-loop experiment also defines the valley (the "overlapped valley") formed by the overlapping first and second sub-valleys. The goal of the computational analysis is to define and isolate the first sub-valley corresponding to the martensite to R-phase transformation using the DSC data corresponding to the second sub-valley and the overlapped valley.

The recorded DSC data consists of x and y data points, where x is temperature in degrees Celsius (° C.) and y is heat flow (enthalpy) in units of watts per gram (W/g). The DSC apparatus includes software such as, for example, Universal Analysis software by TA Instruments, that generates a plot based on the data points. The x and y data may be exported and manipulated mathematically, or the data may be imported into a curve fitting software program that determines equations for curves that fit the data points.

A first computational approach to defining the first sub-valley corresponding to the martensite to R-phase transformation is direct mathematical subtraction. As described above, the double loop experiment allows the second sub-valley to be isolated from the overlapped valley formed upon heating. The data corresponding to the overlapped valley and the second sub-valley is exported out of the DSC software program in an x and y format. Since both the overlapped valley and the second sub-valley have common x (temperature) values, direct subtraction may be used to determine the y (enthalpy) values for the first sub-valley.

The mathematical equations may take the form of:

$$X_{(A+R')} = X_A$$

$$Y_{(A+R')} - Y_A = Y_{R'},$$

where $X_{(A+R')}$ and $X_A$ represent the x values of the overlapped valley and the second sub-valley, respectively, and $Y_{(A+R')}$, $Y_A$, and $Y_{R'}$ represent the y values of the overlapped valley, the second sub-valley and the first sub-valley, respectively. Using the calculated and normalized $Y_{R'}$ (enthalpy) values, the first sub-valley 475 may then be plotted as a function of x (temperature) along with the experimentally-determined overlapped valley 450 and the second sub-valley 480, as shown for example in FIG. 8.

Table 1 shows a portion of DSC data from an exemplary shape memory alloy specimen that has been exported and mathematically subtracted as described above to determine the form of the first sub-valley corresponding to the martensite to R-phase transformation. Only a portion of the data is shown due to the extensive amount of data used to generate DSC curves. The resulting (x,y) values may be fed back into the DSC software program and curves corresponding to the overlapped valley, the first sub-valley and the second sub-valley may be plotted.

TABLE 1

Portion of DSC Data Showing Mathematical Subtraction to Determine First Sub-Peak

| Time Stamp | Temperature | Second Sub-Peak Enthalpy (W/gm) | Overlapped Peak Enthalpy (W/gm) | First Sub-Peak Enthalpy (W/gm) |
|---|---|---|---|---|
| 0.00000000 | −40.00 | −0.03946776 | −0.03993097 | −0.00046320 |
| 0.00333500 | −39.97 | −0.03946850 | −0.03993589 | −0.00046739 |
| 0.00667000 | −39.94 | −0.03946890 | −0.03994082 | −0.00047192 |
| 0.01000500 | −39.90 | −0.03946898 | −0.03994574 | −0.00047677 |
| 0.01333500 | −39.87 | −0.03946883 | −0.03995067 | −0.00048184 |
| 0.01666500 | −39.84 | −0.03946831 | −0.03995563 | −0.00048732 |
| 0.02000000 | −39.80 | −0.03946758 | −0.03996063 | −0.00049305 |
| 0.02333500 | −39.77 | −0.03946659 | −0.03996567 | −0.00049908 |
| 0.02667000 | −39.74 | −0.03946537 | −0.03997067 | −0.00050529 |

TABLE 1-continued

Portion of DSC Data Showing Mathematical Subtraction to Determine First Sub-Peak

| Time Stamp | Temperature | Second Sub-Peak Enthalpy (W/gm) | Overlapped Peak Enthalpy (W/gm) | First Sub-Peak Enthalpy (W/gm) |
|---|---|---|---|---|
| 0.03000000 | −39.70 | −0.03946398 | −0.03997567 | −0.00051169 |
| 0.03333000 | −39.67 | −0.03946243 | −0.03998066 | −0.00051823 |
| 0.03666500 | −39.64 | −0.03946074 | −0.03998566 | −0.00052492 |
| 0.04000000 | −39.61 | −0.03945894 | −0.03999059 | −0.00053165 |
| 0.04334000 | −39.57 | −0.03945699 | −0.03999552 | −0.00053852 |
| 0.04667000 | −39.54 | −0.03945504 | −0.04000044 | −0.00054540 |
| 0.05000000 | −39.51 | −0.03945302 | −0.04000533 | −0.00055231 |
| 0.05333500 | −39.47 | −0.03945096 | −0.04001022 | −0.00055926 |
| 0.05667000 | −39.44 | −0.03944890 | −0.04001507 | −0.00056617 |
| 0.06000000 | −39.41 | −0.03944685 | −0.04001996 | −0.00057311 |
| 0.06334000 | −39.37 | −0.03944475 | −0.04002478 | −0.00058002 |
| 0.06666500 | −39.34 | −0.03944266 | −0.04002963 | −0.00058697 |
| 0.07000000 | −39.31 | −0.03944060 | −0.04003448 | −0.00059388 |
| 0.07333000 | −39.27 | −0.03943854 | −0.04003933 | −0.00060079 |
| 0.07667000 | −39.24 | −0.03943648 | −0.04004433 | −0.00060785 |
| 0.08000000 | −39.21 | −0.03943446 | −0.04004951 | −0.00061506 |
| 0.08333000 | −39.17 | −0.03943244 | −0.04005492 | −0.00062248 |
| 0.08666500 | −39.14 | −0.03943045 | −0.04006051 | −0.00063005 |
| 0.09000000 | −39.11 | −0.03942854 | −0.04006635 | −0.00063781 |
| 0.09333500 | −39.07 | −0.03942670 | −0.04007245 | −0.00064575 |
| 0.09667000 | −39.04 | −0.03942508 | −0.04007870 | −0.00065362 |
| 0.10000000 | −39.01 | −0.03942372 | −0.04008495 | −0.00066123 |
| 0.10333500 | −38.97 | −0.03942273 | −0.04009124 | −0.00066850 |
| 0.10667000 | −38.94 | −0.03942203 | −0.04009749 | −0.00067545 |
| 0.11000000 | −38.91 | −0.03942178 | −0.04010377 | −0.00068200 |
| 0.11333500 | −38.87 | −0.03942181 | −0.04011006 | −0.00068824 |
| 0.11667500 | −38.84 | −0.03942244 | −0.04011638 | −0.00069394 |
| 0.12000000 | −38.81 | −0.03942383 | −0.04012263 | −0.00069879 |
| 0.12333000 | −38.77 | −0.03942619 | −0.04012888 | −0.00070269 |
| 0.12667000 | −38.74 | −0.03942935 | −0.04013509 | −0.00070574 |
| 0.13000000 | −38.71 | −0.03943347 | −0.04014127 | −0.00070780 |

A second approach to defining the first sub-valley is to employ curve fitting software (e.g., Origin 8 data analysis and graphing software from OriginLab) to fit mathematical functions to the data. The functions fit to the second sub-valley and overlapped valley are generally of the same form but include different coefficients that define the shape of each curve. For example, a Voigt function having the following form may be fit to the data:

$$y = y_0 + A \cdot \frac{2\ln 2}{\pi^{3/2}} \frac{w_L}{w_G^2} \cdot \int_{-\infty}^{\infty} \frac{e^{-t^2}}{\left(\sqrt{\ln 2}\, \frac{w_L}{w_G}\right)^2 + \left(\sqrt{4\ln 2}\, \frac{x - x_c}{w_G} - t\right)^2} \, dt$$

Shown in Table 2 below are Voigt function coefficients calculated for the second sub-valley ("A-phase only" data) and the overlapped valley ("A and R-phase" data) of an exemplary shape memory alloy sample, where y0=offset, xc=center, A=amplitude, wG=Gaussian width, and wL=Lorentzian width. Using these parameters, y values can be determined for every value of x.

TABLE 2

Voigt Function Coefficients for Second Sub-Valley and Overlapped Valley

| Data: A and R-phase Model: Voigt Equation: Weighting: | | Data: A-phase only Model: Voigt Equation: Weighting: | |
|---|---|---|---|
| y | No weighting | y | No weighting |
| $\text{Chi}^2/\text{DOF} =$ | 0.00321 | $\text{Chi}^2/\text{DOF} =$ | 0.00168 |
| $R^2 =$ | 0.99723 | $R^2 =$ | 0.98853 |
| y0 | −1.03469 ± 0.00224 | y0 | −1.07514 ± 0.00115 |
| xc | −3.89158 ± 0.00739 | xc | 0.14733 ± 0.01244 |
| A | −66.231 ± 0.22955 | A | −24.52821 ± 0.08735 |
| wG | 9.2719 ± 0.08032 | wG | 1.7494E−7 ± 1804.11958 |
| wL | 6.73491 ± 0.09598 | wL | 10.18019 ± 0.04596 |

Once curves have been fit to the data corresponding to the overlapping valley and the second sub-valley, each of the calculated curves may be integrated to determine the areas under the respective curves. The area calculated for the second sub-valley may then be subtracted from the area calculated for the overlapped valley to obtain the area of the first sub-valley. By taking the derivative of this area, a function representing the form of the first sub-valley may be obtained and plotted. Alternatively, a subtraction approach as described above using the raw data may be employed with the calculated (x,y) values to define the first sub-valley.

Tangent Technique to Determine Phase Transformation Temperatures

Figure 1:
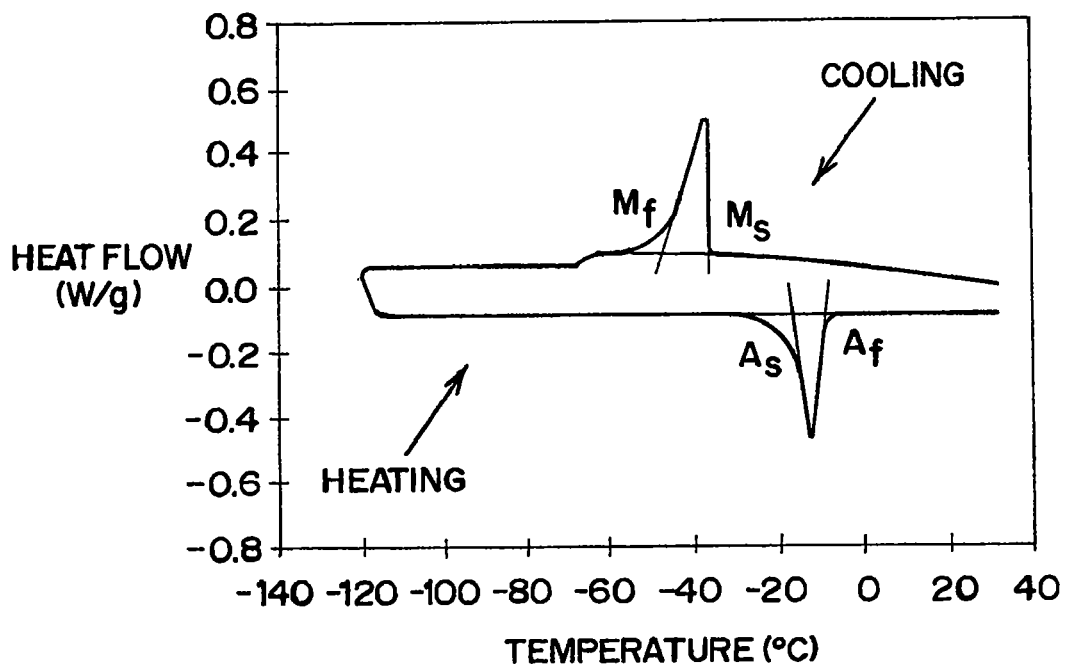
FIG. 1 is a DSC graph for a first exemplary shape memory alloy exhibiting a single-stage transformation.
Figure 2:
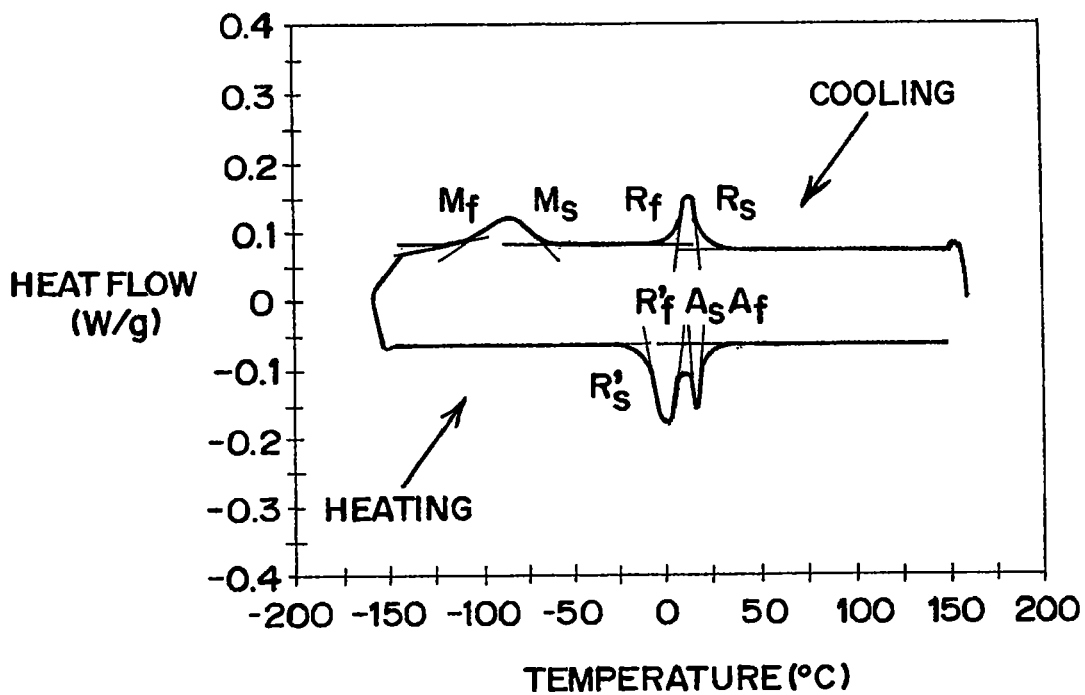
FIG. 2 is a DSC graph for a second exemplary shape memory alloy exhibiting a two-stage transformation.

A tangent technique may be employed to determine the phase transformation temperatures of the shape memory alloy, which generally correspond to the lower and upper boundaries of each peak or valley. Tangent lines are shown for the DSC data presented in FIGS. 1-5. ASTM Standard 2004-05 prescribes drawing the tangents through the inflection points of the peaks or valleys, and obtaining the transformation temperatures (e.g., $M_s$ and $M_f$) as the graphical intersection of the baseline of the DSC data with the extension of the line of maximum inclination. This approach is illustrated in FIGS. 1 and 2. Other tangent line determination approaches may be suitable for particularly broad peaks, where passing the tangent line through the inflection point of the peak or valley skews the results. Software programs, such as TA Instruments' Universal Analysis software, include tangent line determination routines for automatic generation of tangent lines and phase transformation temperatures.

By employing the double-loop DSC experiment described above according to two embodiments, it is possible to isolate the second sub-valley corresponding to the R-phase to austenite phase transformation from the overlapped valley obtained during a conventional single-loop DSC test. Using these DSC data, it is further possible to computationally define the first sub-valley of the overlapped valley corresponding to the martensite to R-phase transformation. Thus, by combining the experimental double-loop method with computational analysis, an overlapped valley may be unambiguously separated into its component first and second sub-valleys. Accordingly, phase transformations for a shape memory alloy exhibiting an R-phase transformation may be properly characterized, and phase transformation temperatures (e.g., $R'_s$, $R'_f$, $A_s$ and $A_f$) may be accurately determined.

While the double-loop experiment described herein has been described in reference to deconvoluting an overlapped valley obtained upon heating a shape memory alloy specimen having an R-phase transformation, the procedure can also be used to deconvolute an overlapped peak that might be obtained upon cooling. For example, the double loop experiment can be applied to a shape memory alloy specimen having an R-phase transformation that exhibits only a single peak upon cooling and two valleys upon heating. In this case, the procedure would entail combining a conventional single-loop DSC experiment with an additional cooling-heating cycle to experimentally define the R-phase to martensite sub-peak in addition to the overlapped peak, followed by computation as described above to isolate the austenite to R-phase peak. The additional cooling-heating cycle would run in reverse of that described above (e.g., the specimen would be heated from a preferably martensitic state to a preferably fully R-phase state with no austenite present, and then cooled to define a sub-peak corresponding only to the R-phase to martensite transformation). As with the embodiments of the double-loop experiment described above, the additional cooling-heating cycle could be performed before or after the conventional single-loop of the double-loop experiment.

It is also noted that the double-loop experiment may be useful for characterizing phase transformations in shape memory materials other than nickel-titanium alloys, such as, for example, copper alloys, e.g., Cu—Zn—Al, Cu—Al—Ni, Cu—Zn—Sn, Cu—Sn, or Cu—Au—Zn; iron alloys, e.g., Fe—Mn, Fe—Mn—Si, Fe—Be, Fe—Pd or Fe—Pt; and other alloys, e.g., Ag—Cd, Au—Cd or In—Ti; and also shape memory polymers.

It is further noted that the double-loop experiment may be applicable to shape memory material characterization techniques other than DSC testing (e.g., electrical resistivity methods, dynamic mechanical analysis, etc.) that involve evaluating data as a function of temperature or stress. For example, instead of heat flow as a function of temperature, the data recorded during the experiment may be displacement as a function of temperature or electrical resistivity as a function of temperature.

Although the present invention has been described in considerable detail with reference to certain embodiments thereof, other embodiments are possible without departing from the present invention. The spirit and scope of the appended claims should not be limited, therefore, to the description of the preferred embodiments contained herein. All embodiments that come within the meaning of the claims, either literally or by equivalence, are intended to be embraced therein.

Furthermore, the advantages described above are not necessarily the only advantages of the invention, and it is not necessarily expected that all of the described advantages will be achieved with every embodiment of the invention.

The invention claimed is:

1. A method of characterizing phase transformations of a shape memory alloy comprising an R-phase transformation, the method comprising:
  recording data from a specimen comprising a shape memory alloy during heating and cooling, the shape memory alloy having an R-phase transformation, the heating and cooling comprising:
  cooling the specimen to a first temperature sufficient to define a first inflection and a second inflection in the data being recorded, the first inflection occurring over a first temperature interval and corresponding to a phase transformation from austenite to R-phase and the second inflection occurring over a second temperature interval and corresponding to a phase transformation from R-phase to martensite;
  heating the specimen to a second temperature sufficient to define a third inflection in the data being recorded, the third inflection occurring over a third temperature interval and being formed by overlapping primary and secondary sub-inflections corresponding respectively to phase transformations from martensite to R-phase and from R-phase to austenite;
  cooling the specimen to a third temperature sufficient to define the first inflection in the data being recorded but not sufficient to define the second inflection, whereby the shape memory alloy has a substantially fully R-phase structure;
  heating the specimen to a fourth temperature sufficient to define the secondary sub-inflection in the data being recorded, the secondary sub-inflection corresponding to the phase transformation from R-phase to austenite.

2. The method of claim 1, wherein the data recorded are heat flow as a function of temperature.

3. The method of claim 1, further comprising, prior to cooling the specimen to the first temperature, heating the specimen to a preheat temperature whereby the shape memory alloy is substantially fully austenitic.

4. The method of claim 1, wherein the third temperature is below a lower boundary of the first temperature interval and above an upper boundary of the second temperature interval.

5. The method of claim 1, wherein each of the first, second, third, and fourth temperatures are maintained for a duration in the range of from about 30 seconds to about 90 seconds.

6. The method of claim 1, furthering comprising determining at least one of an austenite start temperature and an austenite finish temperature of the shape memory alloy from the secondary sub-inflection.

7. The method of claim 6, wherein the secondary sub-inflection comprises a curve having an inflection point, and further comprising forming a tangent line on at least one side of the curve to a baseline of the data to determine at least one of the austenite start temperature and the austenite finish temperature.

8. The method of claim 1, further comprising defining the primary sub-inflection computationally using the third inflection and the secondary sub-inflection.

9. The method of claim 8, wherein the third inflection comprises a set of data points including $Y_{(A+R')}$ values and the secondary sub-inflection comprises a set of data points including $Y_A$ values, and further comprising computing a set of calculated data points for the primary sub-inflection including $Y_{R'}$ values, wherein $Y_{R'}=Y_{(A+R')}-Y_A$, and defining the primary sub-inflection from the calculated data points.

10. The method of claim 8, further comprising subtracting an area of the secondary sub-inflection from an area of the third inflection to determine a primary sub-inflection area, and further comprising taking a derivative of the primary sub-inflection area to define the primary sub-inflection.

11. The method of claim 8, further comprising determining at least one of an R'-phase start temperature and an R'-phase finish temperature of the shape memory alloy from the primary sub-inflection.

12. The method of claim 11, wherein the primary sub-inflection comprises a curve including an inflection point, and further comprising forming a tangent line on at least one side of the curve to a baseline of the data to determine at least one of the R'-phase start temperature and the R'-phase finish temperature.

13. The method of claim 1, wherein cooling the specimen to the third temperature and heating the specimen to the fourth temperature are carried out prior to cooling the specimen to the first temperature and heating the specimen to the second temperature, and further comprising, prior to cooling the specimen to the third temperature, heating the specimen to a preheat temperature whereby the shape memory alloy is substantially fully austenitic.

14. The method of claim 1, further comprising placing the specimen in a device for recording the data, wherein the device is a differential scanning calorimeter and the data recorded are heat flow as a function of temperature, wherein the first inflection is a first peak, the second inflection is a second peak, the third inflection is a valley, and the primary and secondary sub-inflections are first and second sub-valleys, respectively, wherein the first temperature is at least about 10° C. lower than a lower boundary of the second temperature interval, wherein each of the second temperature and the fourth temperature is at least about 10° C. higher than an upper boundary of the third temperature interval, wherein the third temperature is below a lower boundary of the first temperature interval and above an upper boundary of the second temperature interval, further comprising, prior to cooling the specimen to the first temperature, heating the specimen to a preheat temperature whereby the shape memory alloy is substantially fully austenitic, and further comprising determining at least one of an austenite start temperature and an austenite finish temperature of the shape memory alloy from the second sub-valley.

15. The method of claim 14, further comprising defining the first sub-valley computationally using the valley and the second sub-valley, and further comprising determining at least one of an R'-phase start temperature and an R'-phase finish temperature of the shape memory alloy from the first sub-valley.

16. The method of claim 14, wherein cooling the specimen to the third temperature and heating the specimen to the fourth temperature are carried out prior to cooling the specimen to the first temperature and heating the specimen to the second temperature, and wherein heating the specimen to the preheat temperature occurs prior to cooling the specimen to the third temperature.

17. A method of characterizing phase transformations in shape memory materials, the method comprising:
recording data from a shape memory material during heating and cooling, the heating and cooling comprising:
changing the temperature of the specimen in a first direction to a first temperature, the first temperature being sufficient to define a first inflection and a second inflection in the data being recorded, the first inflection occurring over a first temperature interval, and the second inflection occurring over a second temperature interval;
changing the temperature of the specimen in a second direction to a second temperature, the second temperature being sufficient to define a third inflection in the data being recorded, the third inflection occurring over a third temperature interval and being formed by overlapping primary and secondary sub-inflections;
changing the temperature of the specimen in the first direction to a third temperature, the third temperature being sufficient to define the first inflection in the data being recorded but not sufficient to define the second inflection;
changing the temperature of the specimen in the second direction to a fourth temperature, the fourth temperature being sufficient to define the secondary sub-inflection in the data being recorded.

18. The method of claim 17, further comprising defining the primary sub-inflection computationally using the third inflection and the secondary sub-inflection.

\* \* \* \* \*